US010722463B2

(12) United States Patent
Golomb et al.

(10) Patent No.: US 10,722,463 B2
(45) Date of Patent: *Jul. 28, 2020

(54) COMPOSITIONS AND METHODS USING SAME FOR DELIVERING AGENTS INTO A TARGET ORGAN PROTECTED BY A BLOOD BARRIER

(71) Applicant: Zuli Holdings Ltd., Tel Aviv (IL)

(72) Inventors: Gershon Golomb, Efrat (IL); Hila Epstein, Savyon (IL); Eyal Afergan, Kiryat-Yam (IL)

(73) Assignee: Zuli Holdings Ltd., Tel Aviv (IL)

(*) Notice: Subject to any disclaimer, the term of this patent is extended or adjusted under 35 U.S.C. 154(b) by 121 days.

This patent is subject to a terminal disclaimer.

(21) Appl. No.: 15/913,692

(22) Filed: Mar. 6, 2018

(65) Prior Publication Data
US 2018/0193265 A1 Jul. 12, 2018

Related U.S. Application Data

(63) Continuation of application No. 11/921,022, filed as application No. PCT/IL2006/000625 on May 25, 2006, now Pat. No. 9,943,481.

(60) Provisional application No. 60/684,564, filed on May 26, 2005.

(51) Int. Cl.
*A61K 9/127* (2006.01)
*A61K 9/00* (2006.01)

(52) U.S. Cl.
CPC ............ *A61K 9/127* (2013.01); *A61K 9/0019* (2013.01)

(58) Field of Classification Search
None
See application file for complete search history.

(56) References Cited

U.S. PATENT DOCUMENTS

| 4,761,287 A | 8/1988 | Geho |
| 4,804,539 A | 2/1989 | Guo et al. |
| 6,372,250 B1 | 4/2002 | Pardridge |
| 7,122,553 B2* | 10/2006 | Rahman ................ A61K 9/127 514/283 |
| 8,022,279 B2* | 9/2011 | Mayer .................... A61K 9/127 424/450 |
| 9,943,481 B2* | 4/2018 | Golomb ................ A61K 9/127 |

FOREIGN PATENT DOCUMENTS

| WO | WO 91/04014 | 4/1991 |
| WO | WO 94/02178 | 2/1994 |
| WO | WO 98/22092 | 5/1998 |
| WO | WO 03/000174 | 1/2003 |
| WO | WO 2004/087104 A1 | 10/2004 |

OTHER PUBLICATIONS

European Search Report dated May 23, 2012 from corresponding application No. EP 10185543.5, 7 pages.
International Search Report dated Nov. 30, 2006 from corresponding international publication WO 06/126208.
International Preliminary Report on Patentability Chapter 1 dated Nov. 29, 2007 from corresponding international publication WO 06/126208.
Ahl et al., "Enhancement of the In Vivo Circulation Lifetime of L-α-distearoylphosphatidylcholine Liposomes: Importance of Liposomal Aggregation Versus Complement Opsonization", Biochimica et Biophysica Acta (BBA)—Biomembranes, 1329(2): 370-82.
Bauer, et al (2000), "Macrophage-depletion influences the course of murine HSV-1 keratitis", Current Eye Research 20(1):45-53.
Deshpande, et al (Mar. 2004), "Herpetic eye disease: immunopathogenesis and therapeutic measures", Expert Reviews in Molecular Medicine 6(8), 1-14.
Edwards et al., "Role of P-Glycoprotein in Distribution of Nelfinavir across the Blood-Mammary Tissue Barrier and Blood-Brain Barrier," Antimicrobial Agents and Chemotherapy, 49(4): 1626-28, Apr. 2005.
Fromm, Martin F., "Importance of P-Glycoprotein at Blood-Tissue Barriers," TRENDS in Pharmacological Sciences, vol. 25, No. 8, pp. 423-4229, Aug. 2004.
Huitinga et al., "Macrophages in T cell line-mediated, demyelinating, and chronic relapsing experimental autoimmune encephalomyelitis in Lewin rats," Clin. Exp. Immunol 1995; 100:344-351.
Huitinga et al., "Suppression of Experimental Allergic Encephalomyelitis in Lewis Rats After Elimination of Macrophages", Journal of Experimental Medicine, 172: 1025-1033, 1990.
Immordino et al., "Stealth Liposomes: review of the basic science, rationale, and clinical applications, existing and potential", International Journal of Nanomedicine 2006: 1(3) pp. 297-315, 2006.
Kamimura et al., "Barrier Function of Microvessels and Roles of Glial Cell Line-Derived Neurotrophic Factor in the Rat Testis," Med Electron Microsc (2002) 35:139-145.
Larkin, et al (1997), "Infiltrating inflammatory cell phenotypes and apoptosis in rejected human corneal allografts", Eye 11:68-74.
Li et al. (2006) "B Lymphocytes from early vertebrates have potent phagocytic and microbicidal abilities", Nature Immunology: 7(10): 1116-24.
Pelletier, et al., "The Blood-Testis Barrier and Sertoli Cell Junctions: Structural Considerations," Microscopy Research and Techniques, 20(1): 3-33, Jan. 1992. Abstract Only.
Reinhard, et a. (2001), "Immune cells in the anterior chamber of patients with immune reactions after penetrating keratoplasty", Cornea (21(1): 5-61.

(Continued)

Primary Examiner — Robert M Kelly
(74) Attorney, Agent, or Firm — Cadwalader, Wickersham & Taft LLP

(57) ABSTRACT

A method of delivering a pharmaceutical agent into a target organ protected by a blood barrier is provided. The method comprising administering to a subject in need thereof an amount of liposomes which comprise the pharmaceutical agent, the amount and the liposomes are selected such that the liposomes accumulate in cells of an immune system of the subject to thereby generate liposome loaded immune cells, the liposome loaded immune cells become activated and cross the blood barrier, and an effective amount of the pharmaceutical agent is released from the liposomes in the target organ of the subject.

10 Claims, 15 Drawing Sheets

(56) References Cited

OTHER PUBLICATIONS

Rousseau et al., "Early Detection of Liposome Brain Localization in Rat Experimental Allergic Encephalomyelitis", Exp. Brain Res., 125:255-264, 1999.
Saatov et al., "Autologous Liposomes", Vestin Akad Med Nauk SSSR, 1990 (8): 47-50, Abstract Only.
Steuer et al., "Functional Characterization and Comparison of the Outer Blood-Retina Barrier and the Blood-Brain Barrier," Investigative Ophthalmology & Visual Science, vol. 46, No. 3, pp. 1047-1053, Mar. 2005.
Stewart et al., "Blood-Eye Barriers in the Rat: Correlation of Ultrastructure with Function," The Journal of Comparative Neurology, 340 (4): 566-76, Oct. 9, 2004, (Abstract Only).
Szebeni et al., "Liposome-Induced Pulmonary Hypertension: Properties and Mechanism of a Complement-Mediated Pseudoallergic Reaction", Heart and Circulatory Physiology, 279(3): H1319-28.
Office Actions and Response for related U.S. Appl. No. 11/921,022, filed Oct. 6, 2009 and issued as U.S. Pat. No. 9,943,481 dated Apr. 17, 2018.
Notice of Allowance and Examiner Initiated Interview Summary dated Dec. 23, 2017.
Response to Final Rejection dated Oct. 24, 2017.
Final Rejection dated Aug. 30, 2017.
Amendment and Response to Non-Final Rejection dated Jul. 19, 2017.
Non-Final Rejection dated Apr. 19, 2017.
Amendment and Reponse to Final Rejection with Request for Continued Examination and Extension of Time dated Feb. 13, 2017.
Advisory Action dated Jan. 19, 2017.
Response to Final Rejection dated Dec. 12, 2016.
Final Rejection and Applicant Initiated Interview Summary dated Oct. 13, 2016.
Final Rejection dated Aug. 30, 2016.
Supplemental Amendment and Reponse to Non-Final Rejection dated Jun. 28, 2016.
Notice of Non-Complaint Amendment dated Jun. 8, 2016.
Response to Non-Final Rejection dated Mar. 31, 2016.
Applicant Initiated Interview Summary dated Mar. 10, 2016.
Non-Final Rejection dated Dec. 4, 205.
Amendment and Response to Final Rejection with Request for Continued Examination dated Oct. 5, 2015.
Final Rejection dated Jul. 23, 2015.
Amendment and Response to Non-Final Rejection with Extension of Time dated May 15, 2015.
Non-Final Rejection dated Jan. 15, 2015.
Amendment and Response to Final Rejection with Request for Continues Examination and Extension of Time dated Sep. 9, 2014.
Final Rejection dated May 15, 2014.
Amendment and Response to Non-Final Rejection dated Mar. 17, 2014.
Non-Finial Rejection dated Dec. 19, 2013.
Amendment and Reponse to Final Rejection with Request for Continued Examination and Extension of Time dated Oct. 12, 2012.
Final Rejection dated Jun. 14, 2012.
Amendment and Response to Non-Final Rejection dated Apr. 26, 2012.
Non-Final Rejection dated Feb. 3, 2012.
Response to Election/Restriction Requirement dated Dec. 12, 2011.
Requirement for Restriction/Election dated Nov. 15, 2011.
Supplemental Preliminary Amendment dated Sep. 28, 2010; and.
Preliminary Amendment dated Jun. 2, 2010.

\* cited by examiner

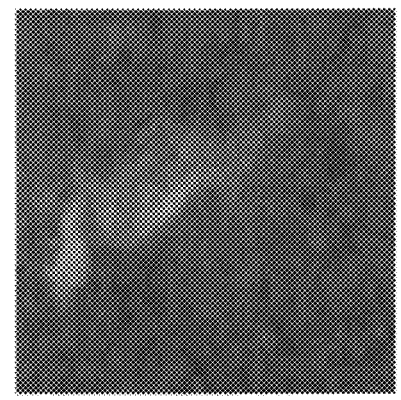
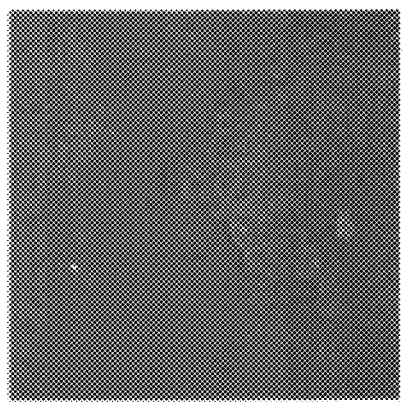
FIGs. 2a-b

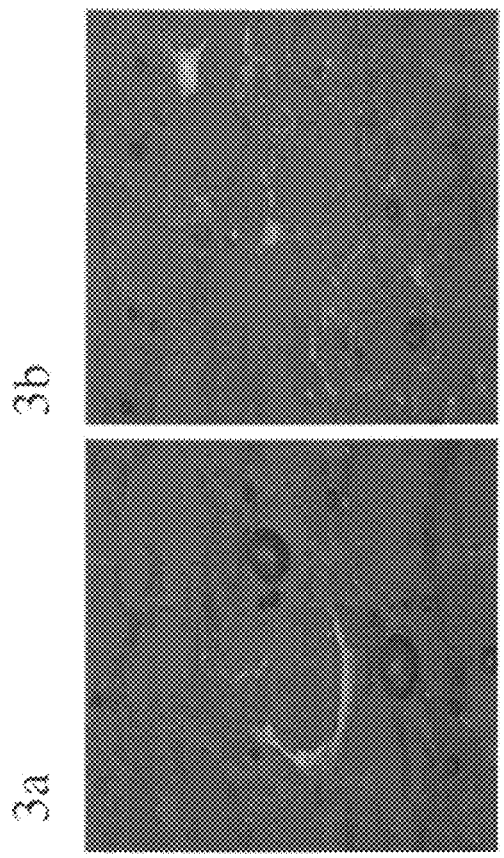
FIGs. 3a-b

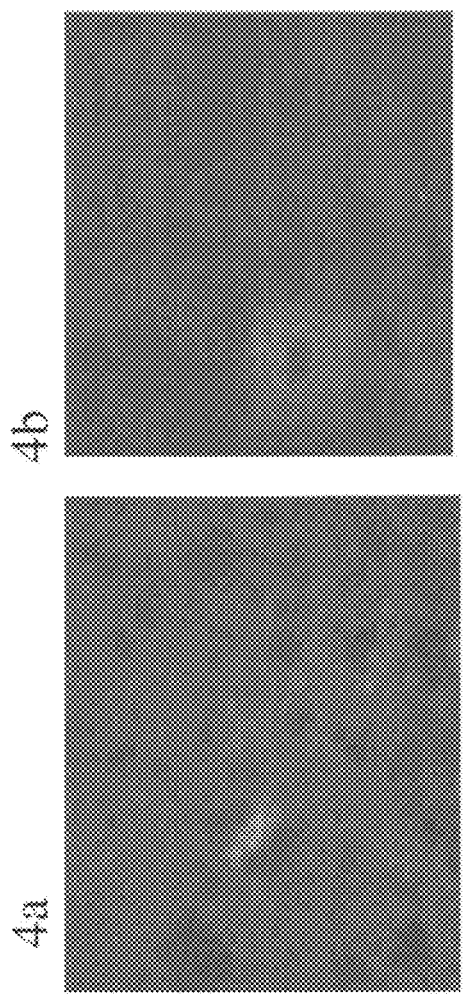
FIGs. 4a-b

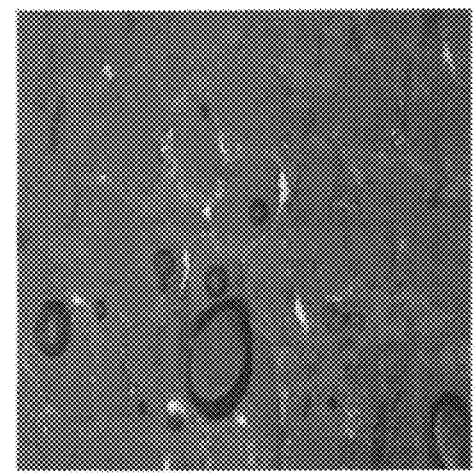
FIGs. 5a-b

FIGs. 6a-b

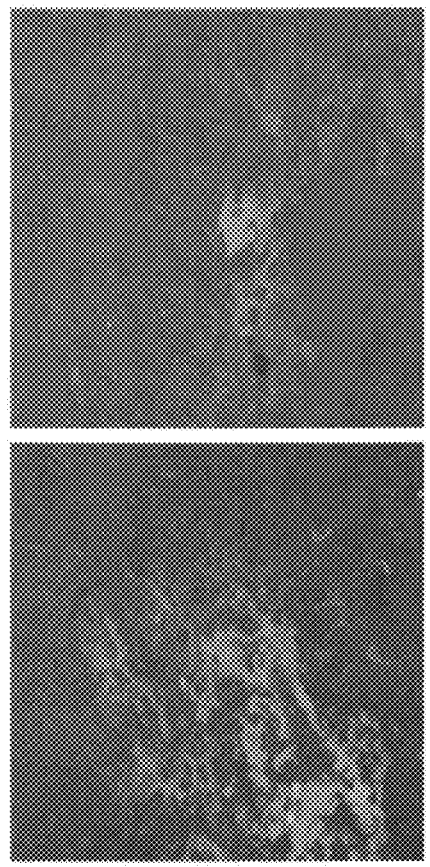
FIGs. 7a-b

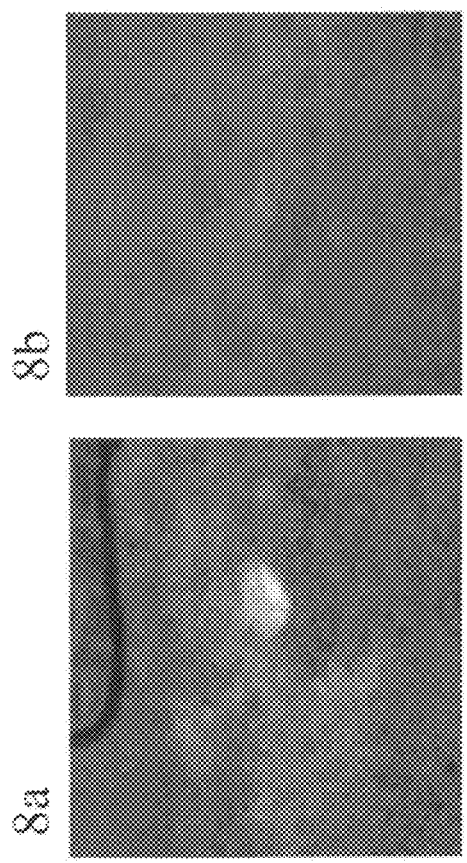
FIGs. 8a-b

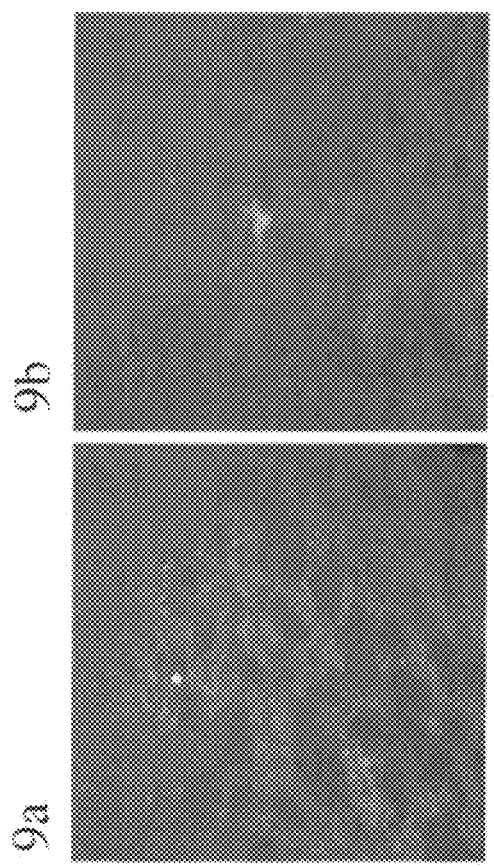
FIGs. 9a-b

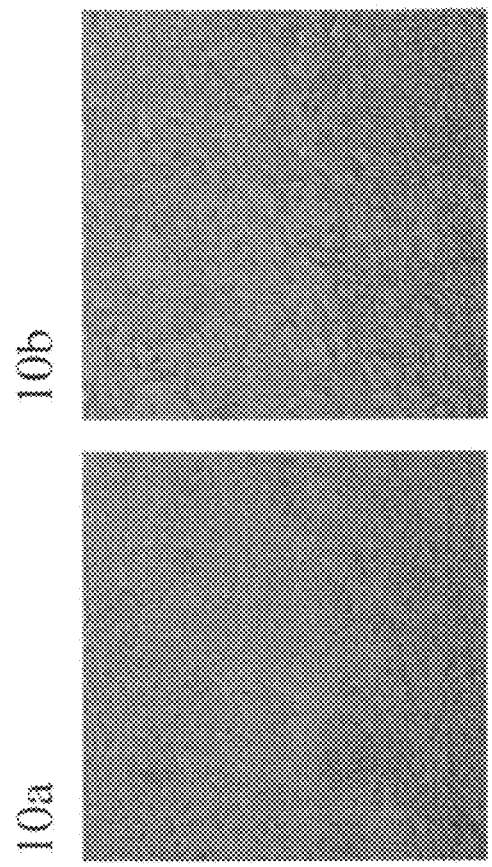
FIGs. 10a-b

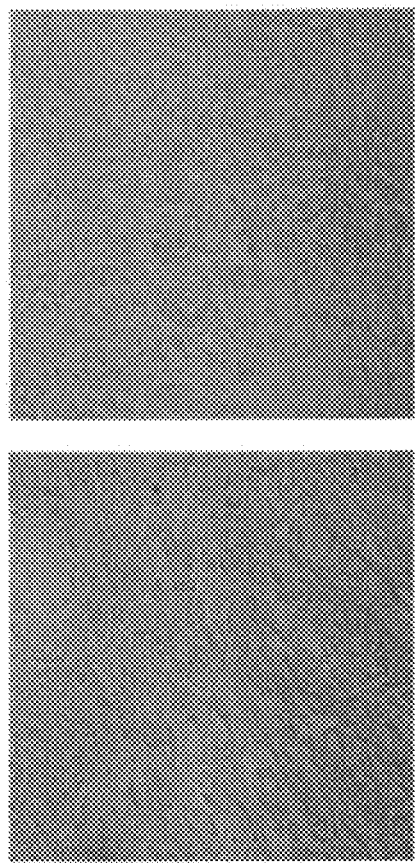
FIGs. 11a-b

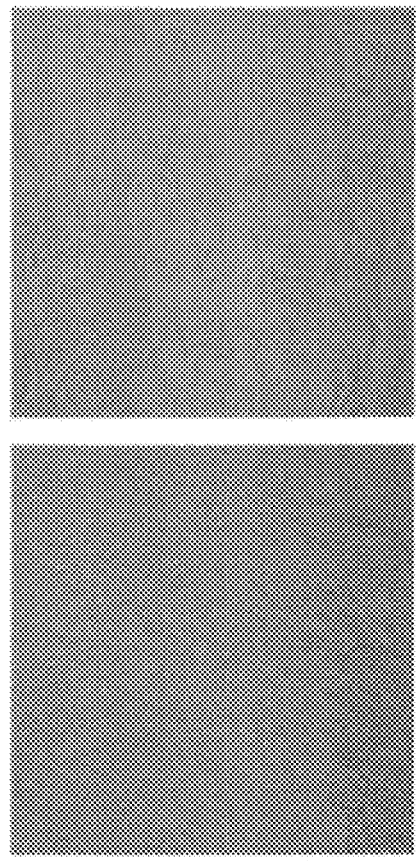
FIGs. 12a-b

FIGs. 13a-b
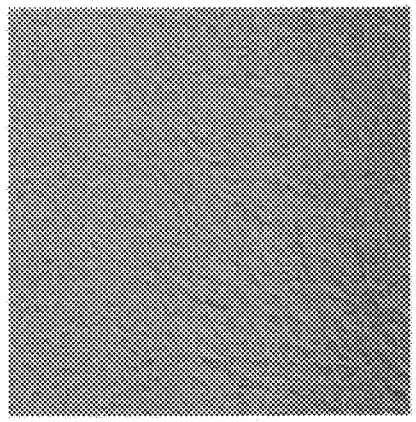
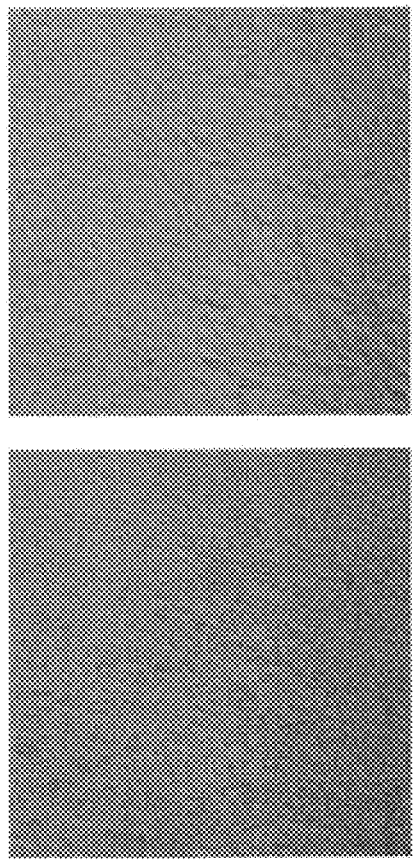

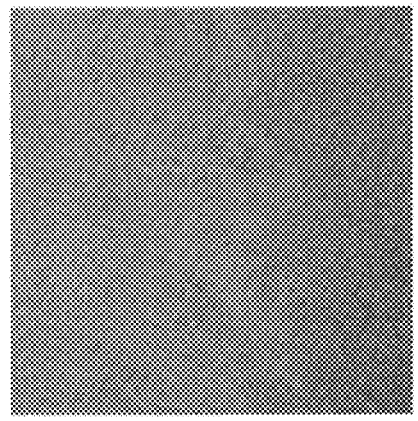
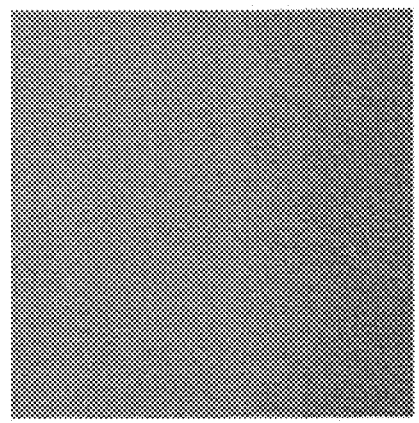
FIGs. 14a-b

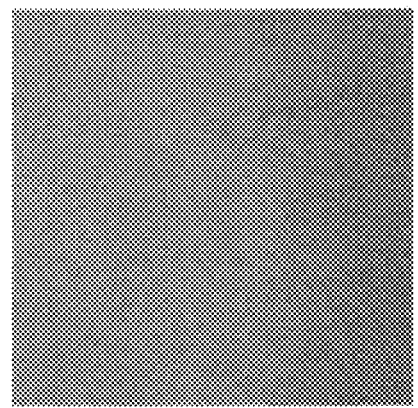
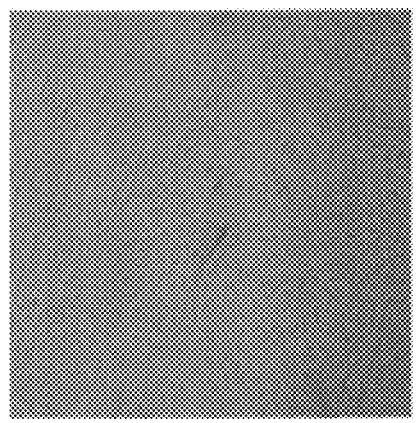
FIGs. 15a-b

COMPOSITIONS AND METHODS USING SAME FOR DELIVERING AGENTS INTO A TARGET ORGAN PROTECTED BY A BLOOD BARRIER

RELATED APPLICATIONS

This application is a continuation of U.S. patent application Ser. No. 11/921,022 filed Oct. 6, 2009 and granted as U.S. Pat. No. 9,943,481 on Apr. 17, 2018, which is a National Stage Entry of PCT Patent Application No. PCT/IL2006/000625 having an international filing date of May 25, 2006, which claims the benefit of the U.S. Provisional Patent Application No. 60/684,564 filed on May 26, 2005. The contents of the above Applications are all incorporated herein by reference.

FIELD AND BACKGROUND OF THE INVENTION

The present invention relates to methods and pharmaceutical compositions for delivering a pharmaceutical agent into a target organ which is protected by a blood barrier and, more particularly, to the delivery of pharmaceutical agents to the brain.

While the invention will be described herein in more detail with respect to delivery of pharmaceutical agents to the brain, it is to be understood that the invention is applicable for delivery of pharmaceutical agents to any organ protected by a barrier.

There are four known mammalian blood barriers including the blood brain barrier (BBB), the blood retinal barrier, the blood testes barrier and the blood mammary gland barrier. All of these function to separate the organ or tissue from features in the periphery, allowing only selective transport of factors. Structurally, these barriers are characterized by tight junctions between the cells and are all endowed with several specific markers such as the glucose transporter, P-glycoprotein, and γ glutamyl transpeptidase. The barriers also contain a paucity of endocytic vesicles within them and the presence of the molecules that regulate the ionic and metabolic gradients that constitute the barrier.

Delivery of many therapeutic agents, particularly nonlipophilic drugs, to these four organs is restricted by their respective barriers.

Over the years, several strategies to circumvent the BBB have been proposed, such as by transient osmotic opening of the BBB, high dosing (e.g., of chemotherapy), use of carrier systems such as antibodies, or even biodegradable implants. However, some of these methods are associated with two major pitfalls: they are invasive procedures and they are relatively inefficient, resulting in only superficial distribution of the drug in the brain. High dosing of pharmaceutical agents to overcome this inefficiency leads to an increase in serious potential side effects. An alternative strategy of delivering drugs across the BBB is by administering their lipophilic precursors (i.e., pro-drugs). However, increased lipophilicity tends to increase uptake by other tissues with resultant toxicity.

Several synthetic NP polymers, arranged as spheres have been studied as carriers of drugs across the BBB. Poly(butyl cyanoacrylate) has been reported to effectively deliver different drugs, including peptides [Kreuter J. Adv. Drug Delivery Rev. 2001, 47:65-81; Gulayev A E, et al., Pharm Res 1999, 16:1564-9]. The formulation efficiency has been attributed to a detergent Tween 80 (polysorbate) coating, which may prevent NP aggregation and delay NP removal by the Mononuclear Phagocyte System (MPS, formerly known as the RES, reticuloendothelial system) [Kreuter J. Adv. Drug Delivery Rev. 2001, 47:65-81; Troster S D et al., Int. J. Pharm. 1990, 61:85-100]. While the exact mechanism of NP brain delivery is unknown, it has been suggested that brain delivery by NPs might be mediated simply by the disruption of the BBB by surfactants i.e., detergents [Lockman P R, et al. Pharm Res 2003; 20:705-13; Olivier J C et al., Pharmaceutical Research 1999; 16:1836-42].

However, recent studies suggest that the effect of polysorbate 80 is unrelated to BBB toxicity, but is rather due to adsorption of blood apolipoproteins, such as apolipoprotein E onto the nanoparticle surface. The particles subsequently appear to mimic low density lipoprotein (LDL) particles and can thereby interact with the LDL receptor leading to their uptake by the endothelial cells via receptor-mediated endocytosis [Kreuter J, et al., Pharm. Res. 2003; 20:409-16; Kreuter J. et al., J. Drug Targeting 2002; 10:317-25]. Other mechanisms such as tight junction modulation or P-glycoprotein inhibition also may occur. Moreover, these mechanisms may run in parallel or may be cooperative thus enabling drug delivery to the brain.

It has also been suggested that liposomes can enhance drug delivery to the brain across the blood-brain barrier [Umezawa and Eto, Biochem Biophys Res. Comm. 153: 1038-1044 (1988); Chan et al., Ann. Neurol, 21:540-547 (1987); Laham et al., Life Sciences 40:2011-2016 (1987); and Yagi et al., J. APRlo Biocheme 4:121-125 (1982)]. Liposomes are small vesicles (usually submicron sized) comprised of one or more concentric bilayers of phospholipids separated by aqueous compartments. There is, however, conflicting evidence whether liposomes may be used to enhance the uptake of drugs into the brain. In some cases, it has been shown that liposomes do not cross the blood-brain barrier [Schackert et al., Select. Cancer TheraReut., 5:73-79 (1989) and Micklus et al., Biochem Biophys Acta 1124:7-12 (1992)]. Micklus notes that liposomes circulating in the plasma are ultimately taken up by the liver, digested and the lipid components released and redistributed to other organs [Derksen et al., Biochim. Biophys Acta 971:127-136 (1988)]. The radioactivity found in the brain following intravenous injection of labeled liposomes of Umezawa and Eto, and others may in fact be derived from digested lipids and not from the intact liposomes themselves.

In several cases where liposomes were shown to cross the BBB, the permeability of the BBB itself was disrupted [Rousseau et al., 1997, Magma 5 213-22; Rousseau et al., 1999, Experimental brain research; Experimentelle Hirnforschung; Experimentation cerebrale 125 (1999) 255-64; Stavaraky et al., Magn Reson Imaging 11 (1993) 685-9]. Thus, in these cases the penetration of the liposomes through the BBB cannot be attributed to the liposomes themselves but rather to the disrupted properties of the barrier.

It has been suggested that the use of an external ligand such as mannose can improve a liposomal particle's ability to cross the BBB [Huitinga et al., J exp Med 172 (1990) 1025-33; Umezawa F., Biochem Biophys Res Commun 153 (1988) 1038-44]. A possible penetration mechanism could be that BBB cells and glial cells recognize mannose molecules on the liposome membrane surface. Indeed, the research by Huitinga suggests that only mannosylated liposomes are able to cross the BBB since non-mannosylated liposomes could not penetrate the barrier. It should be noted, that the mannosylated liposomes that were able to cross the barrier remained localized to this area and were not detected in other brain areas [Huitinga et al., 1995, Clin Exp Immunol 100, 344-51]. Also, the mannosylated liposomes were shown to be incorporated in glial cells as opposed to neuronal cells, the former having a receptor for mannose [Umezawa F., Biochem Biophys Res Commun 153, 1988, 1038-44]. PCT Application, Publication No. WO9402178A1 to Micklus discusses the coupling of liposomes to an antibody binding fragment which binds to a receptor molecule present on the vascular endothelial cells of the mammalian blood-brain barrier.

In conclusion, from the presented evidence it remains unclear whether unmodified liposomes are able to cross an undisrupted blood brain barrier, although the use of liposomes modified with external ligands such as mannose and antibody binding fragments do appear to enhance liposome penetration.

Until recently, the brain was considered an immunologically privileged organ [Miller D W, J Neurovirol 1999; 5:570-8]. This was based on early studies that found few antigen-presenting cells in the central nervous system. In addition, there was a perceived lack of a lymphatic system within the brain to carry immunogenic material in the central nervous system to lymph nodes where a humoral immune response could be initiated. The presence of the BBB was thought to prevent the entry of immune cells from the peripheral circulation into the brain. However, there is increasing evidence suggesting that the brain is under immunological surveillance. It has been documented that monocytes, and lymphocytes (T and B) both cross the BBB [Andersson et al, 1992, Neuroscience 48: 169±186; Nottet et al, 1996, J Immunol 156: 1284±1295; Hickey et al, 1991, J Neurosci Res 28: 254±260; Knopf et al, 1998, J Immunol 161: 692±701]. Such studies have necessitated a re-thinking of the role of the BBB in immune cell trafficking into the central nervous system.

An important part of the body's defense of bacterial or viral infections is the ability of monocytes and granulocytes to invade the tissue and begin phagocytosis of the foreign material. Indeed, infiltration of monocytes and neutrophils from the bloodstream into the infected tissue is part of the initial immune response. However, there are notable differences in the penetration of monocytes and neutrophils in the BBB and the peripheral microvasculature. First, trafficking of activated leukocytes across the BBB display differences that are dependent on cell type, with monocytes being more capable than neutrophils in passing through the BBB. This was demonstrated in mice injected with various pro-inflammatory stimuli directly into the hippocampus [Andersson et al, 1991, Neuroscience, 42, 169-186; Andersson et al., 1992, Neuroscience 48, 169-182]. Under normal homeostatic conditions, minimal margination and diapedisis (i.e., movement from blood vessels to tissues) of both neutrophils and monocytes was observed in the BBB. Following hippocampal injection of kianic acid or LPS challenge, a dramatic increase in the margination of neutrophils and monocytes to the brain endothelial cells was seen [Andersson et al, 1991, Neuroscience, 42, 169-186; Andersson et al., 1992, Neuroscience 48, 169-182]. Although there was an increased attachment of both neutrophils and monocytes to the brain endothelial cells, only the monocytes underwent diapedisis and were able to move through the BBB into the brain. Infiltration of neutrophils through the BBB was only observed following breakdown of BBB integrity, and was in contrast to the rapid and substantial accumulation of neutrophils observed in the CSF through the choriod plexus [Andersson et al, 1991, Neuroscience, 42, 169-186; Andersson et al., 1992, Neuroscience 48, 169-182]. The relative inability of neutrophils to move across the BBB, suggests that it is the initial monocyte response that is the important mediator of the immune response in the CNS. The observation that the number of macrophage cells in the brain (following LPS injection) was reduced when peripheral circulating monocytes were depleted, suggests that a significant number of the macrophages in the brain parenchyma were attributable to the infiltration of monocytes across the BBB [Andersson et al., 1992, Neuroscience 48, 169-182].

Transport of the immune cells into the CNS is attributed in part, to the adhesion molecules found in the vascular endothelial cells that form the BBB. Some of these adhesion molecules, like the cadherins, are involved in the formation of intercellular tight junction complexes between the brain microvessel endothelial cells.

It should be noted that leukocyte transendothelial migration across an altered BBB is a prominent feature of many neurodegenerative disorders. Marked changes in BBB function is observed in several neurological disorders associated with immune responses such as multiple sclerosis (MS), meningitis, and HIV-1-associated dementia.

It is well known that cells belonging to the MPS, including monocytes and macrophages, are able to phagocytose particles such as liposomes. Surface charge, size, concentration and composition are all known to influence the cell's ability for phagocytosis. According to some research, negatively charged liposomes associate more effectively with the phagocytic cells [Raz, A., et al., 1981, Cancer Research 41, 487-494; Hsu, M., et al., (1982) Biochem. Biophys. Acta 720, 411-419] and large-sized liposomes (above 500 nm) are also phagocytized more efficiently. The use of PEG linked to the lipids comprising the liposomal membrane prevents uptake by the phagocytic cells such that cationic liposomes without PEG are taken up by the reticuloendothelial system (RES) at a much higher rate than PEGylated cationic liposomes are. The same is true for sterically shielded lipids such as ganglioside-$GM_1$ and phosphatidylinositol. Liposomes containing negatively charged lipids that are not sterically shielded (phosphatidylserine, phosphatidic acid, and phosphatidylglycerol) are phagocytosed more readily. Liposomes containing sterically shielded lipids are cleared even more slowly than neutral liposomes [Gabizon A., Papahadjopoulos D. Biochim. Biophys. Acta, 1103: 94-100, 1992]. On the other hand, inclusion of cholesterol in the liposome enhances uptake by the MPS [Ahsan, F. et al., 2002, Journal of controlled Release, 79, 29-40].

It has been suggested that liposomes may cross a disrupted blood brain barrier using a "particle pick-up" mechanism by circulating macrophages [Rousseau et al., 1999, Experimental brain research; Experimentelle Hirnforschung; Experimentation cerebrale 125 (1999) 255-64]. However, the mechanism is dismissed (by the authors themselves) because of the short delay between liposome injection and brain localization as assessed by scintigraphy. If circulating macrophages did indeed capture the liposomes, this would take time to occur and brain activity would progressively increase, which was not the case in Rousseau's findings. Of note, the formulation and size of liposomes used in this study were not selected to encourage phagocytosis by cells of the MPS which also suggests that the liposomes of this study were unlikely to cross the BBB via a macrophages pick-up mechanism. Also, Rousseau envisaged using liposomes to cross the BBB as a diagnostic tool only and not as a therapeutic aid.

In a research carried out by Huitinga et al., [J Exp Med 172 (1990) 1025-33], it is suggested that mannosylated liposomes may cross the blood brain barrier via activated monocytes. He suggests that mannosyl receptors can be expressed on activated monocytes leading to a more efficient in vitro binding of mannosylated liposomes to macrophages. However, this explanation contradicts his findings since, whereas both mannosylated and non-mannosylated liposomes were incorporated in monocytes in the spleen and liver equally well, only the modified liposomes could penetrate the BBB.

In both the studies carried out by Roussea et al, 1999 supra and Huitinga et al, 1999 supra the liposomes were confined to the BBB area and did not move out to other brain areas.

U.S. Pat. Application No. 20050048002 to Barrett discusses the use of phagocytic cells as carriers of particles to the brain, but does not discuss using phagocytic cells as transporters of particles to other organs protected by a barrier including the eye, testicles and mammary gland. Barrett et al., does not relate at all to the use of liposomes as carriers, but rather to solid particles (e.g. a microparticle or nanoparticle) between 150 nm to 100 μm. Barrett et al., does not relate to methods of enhancing uptake by phagocytic cells such as by using negatively charged particles. Indeed, Barrett specifies pegylated phospholipids and sterically shielded lipids (as a surfactant only) both of which are known to prevent uptake by phagocytic cells.

U.S. Pat. Application No. 20040266734 and U.S. Pat. Application No. 20040265391 both describe liposomes of a similar formulation to that of the present invention containing an agent which is toxic to MPS for the treatment of restenosis and acute coronary syndromes, thereby teaching away from the present invention.

In summary, the mechanism of "liposome pick up" by circulating macrophages has been discussed with reference to either a disrupted blood brain barrier or mannosylated liposomes. In both of these the mechanism was deemed unlikely. When discussed in U.S. Pat. Application No. 20050048002, liposomes are not mentioned and the only reference to lipid substances relates to surfactants which may prevent effective uptake by phagocytic cells if pegylated or shielded as described therein.

In view of the above, there is a widely recognized need for and it would be highly advantageous to have an improved method of delivering therapeutic and diagnostic agents across blood barriers and into target tissues.

SUMMARY OF THE INVENTION

It is an object of the present invention to provide methods for delivering a pharmaceutical agent into a target organ protected by a blood barrier.

It is another object of the present invention to provide a pharmaceutical composition for crossing a blood barrier of a target organ.

It is yet another object of the present invention to provide methods for delivering a pharmaceutical agent through a blood brain barrier and into a brain.

Hence, according to the present invention there is provided a method of delivering a pharmaceutical agent into a target organ protected by a blood barrier, the method comprising administering to a subject in need thereof an amount of liposomes which comprise the pharmaceutical agent, the amount and the liposomes are selected such that the liposomes accumulate in cells of an immune system of the subject to thereby generate liposome loaded immune cells, the liposome loaded immune cells become activated and cross the blood barrier, and an effective amount of the pharmaceutical agent is released from the liposomes in the target organ of the subject.

According to another aspect of the present invention there is provided a pharmaceutical composition for crossing a blood barrier of a target organ, the pharmaceutical composition comprising as an active ingredient liposomes designed to accumulate in, and activate cells of an immune system to cross the blood barrier of the target organ, the liposomes comprise a pharmaceutical agent.

According to yet another aspect of the present invention there is provided a method of delivering a pharmaceutical agent through a blood brain barrier and into a brain, comprising administering to a subject in need thereof an amount of liposomes which comprise the pharmaceutical agent, the amount and the liposomes are selected such that the liposomes accumulate in cells of an immune system of the subject to thereby generate liposome loaded immune cells, the liposome loaded immune cells become activated and cross the blood brain barrier, and an effective amount of the pharmaceutical agent is released from the liposomes in the brain.

According to further features in preferred embodiments of the invention described below, the target organ is selected from the group consisting of brain, an eye, a mammary gland and a testicle.

According to still further features in the described preferred embodiments, the target organ is brain.

According to still further features in the described preferred embodiments, the blood barrier is not disrupted.

According to still further features in the described preferred embodiments, the liposomes are non-mannosylated.

According to still further features in the described preferred embodiments, the pharmaceutical agent is encapsulated within the liposomes.

According to still further features in the described preferred embodiments, the pharmaceutical agent is adsorbed on a surface of the liposomes.

According to still further features in the described preferred embodiments, the administering is selected from the group consisting of intravenous (IV) administration, intrarterial (IA) administration, intramuscular (IM) administration, subcutaneous (SC) administration and intraperitoneal (IP) administration.

According to still further features in the described preferred embodiments, the liposomes have a charged surface.

According to still further features in the described preferred embodiments, the charged surface is a negatively charged surface.

According to still further features in the described preferred embodiments, the negatively charged surface comprises negatively charged phospholipids.

According to still further features in the described preferred embodiments, the negatively charged phospholipids are selected from the group consisting of phosphatidylserine, phosphatidic acid, phosphatidylcholine and phosphatidyl glycerol.

According to still further features in the described preferred embodiments, the liposomes are about 0.05-1.0 μm in diameter.

According to still further features in the described preferred embodiments, the cells of an immune system are cells of a mononuclear phagocytic system.

According to still further features in the described preferred embodiments, the cells of a mononuclear phagocytic system are selected from the group consisting of macrophages and monocytes.

According to still further features in the described preferred embodiments, the pharmaceutical agent is a therapeutic agent or a diagnostic agent.

According to still further features in the described preferred embodiments, the therapeutic agent is selected from the group consisting of an antibiotic agent, an analeptic agent, an anti-convulsant agent, an anti-neoplastic agent, an anti-inflammatory agent, an antiparasitic agent, an antifungal agent, an antimycobacterial agent, an antiviral agent, an antihistamine agent, an anticoagulant agent, a radiotherapeutic agent, a chemotherapeutic agent, a cytotoxic agent, a neurotrophic agent, a psychotherapeutic agent, an anxiolytic sedative agent, a stimulant agent, a sedative agent, an analgesic agent, an anesthetic agent, a vasodilating agent, a birth control agent, a neurotransmitter agent, a neurotransmitter analog agent, a scavenging agent, a fertility-enhancing agent and an anti-oxidant agent.

According to still further features in the described preferred embodiments, the neurotransmitter agent is selected from the group consisting of acetycholine, dopamine, norepinephrine, serotonin, histamine, epinephrine, Gamma-aminobutyric acid (GABA), glycine, glutamate, adenosine, inosine and aspartate.

According to still further features in the described preferred embodiments, the therapeutic agent is a protein.

According to still further features in the described preferred embodiments, the therapeutic agent is a peptide.

According to still further features in the described preferred embodiments, the protein is selected from the group consisting of an enzyme, a growth factor, and an antibody.

According to still further features in the described preferred embodiments, the peptide is a neuropeptide.

According to still further features in the described preferred embodiments, the neuropeptide is selected from the group consisting of Oxytocin, Vasopressin, Corticotropin releasing hormone (CRH), Growth hormone releasing hormone (GHRH), Luteinizing hormone releasing hormone (LHRH), Somatostatin growth hormone release inhibiting hormone, Thyrotropin releasing hormone (TRH), Neurokinin α (substance K), Neurokinin β, Neuropeptide K, Substance P, β-endorphin, Dynorphin, Met- and leu-enkephalin, Neuropeptide tyrosine (NPY), Pancreatic polypeptide, Peptide tyrosine-tyrosine (PYY), Glucogen-like peptide-1 (GLP-1), Peptide histidine isoleucine (PHI), Pituitary adenylate cyclase activating peptide (PACAP), Vasoactive intestinal polypeptide (VIP), Brain natriuretic peptide, Calcitonin gene-related peptide (CGRP) (α- and β-form), Cholecystokinin (CCK), Galanin, Islet amyloid polypeptide (IAPP), Melanin concentrating hormone (MCH), ACTH, α-MSH, Neuropeptide FF, Neurotensin, Parathyroid hormone related protein, Agouti gene-related protein (AGRP), Cocaine and amphetamine regulated transcript (CART)/peptide, Endomorphin-1 and -2, 5-HT-moduline, Hypocretins/orexins Nociceptin/orphanin FQ, Nocistatin, Prolactin releasing peptide, Secretoneurin and Urocortin According to still further features in the described preferred embodiments, the therapeutic agent is a nucleic acid.

According to still further features in the described preferred embodiments, the therapeutic agent is a small molecule having a molecular mass of less than 1000 Da.

According to still further features in the described preferred embodiments, the diagnostic agent is a contrast agent.

According to still further features in the described preferred embodiments, the contrast agent is selected from the group consisting of an X-ray imaging contrast agent, a magnetic resonance imaging contrast agent and an ultrasound imaging contrast agent.

According to still further features in the described preferred embodiments, the diagnostic agent is a radioimaging agent or a fluorescence imaging agent.

According to still further features in the described preferred embodiments, the pharmaceutical agent is selected to treat or diagnose a brain indication.

According to still further features in the described preferred embodiments, the brain indication is selected from the group consisting of brain tumor, neuropathy, Alzheimer's disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, bacterial infection, fungal infection, stroke, aging, dementia, schizophrenia, depression, manic depression, anxiety, panic disorder, social phobia, sleep disorder, attention deficit, conduct disorder, hyperactivity, personality disorder, drug abuse, infertility and head injury.

The present invention provides novel compositions and methods of using same for delivery of pharmaceutical agents to blood barrier protected organs.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIGS. 2a-b are images captured by confocal microscopy of brain sections one hour following rhodamine DSPE liposome administration.

FIGS. 3a-b are images captured by confocal microscopy of brain sections four hours following rhodamine DSPE liposome administration.

FIGS. 4a-b are images captured by confocal microscopy of brain sections one hour following 1-Hydroxypyrene-3,6,8-Trisulfonic acid liposome administration.

FIGS. 5a-b are images captured by confocal microscopy of brain sections four hours following 1-Hydroxypyrene-3,6,8-Trisulfonic acid liposome administration.

FIGS. 6a-b are images captured by confocal microscopy of spinal cord sections one hour following rhodamine DSPE liposome administration.

FIGS. 7a-b are images captured by confocal microscopy of spinal cord sections four hours following rhodamine DSPE liposome administration.

FIGS. 8a-b are images captured by confocal microscopy of spinal cord sections one hour following 1-Hydroxy-pyrene-3,6,8-Trisulfonic acid liposome administration.

FIGS. 9a-b are images captured by confocal microscopy of spinal cord sections four hours following 1-Hydroxy-pyrene-3,6,8-Trisulfonic acid liposome administration.

FIGS. 10a-b are images captured by confocal microscopy of brain sections four hours following intravenous (I.V.) administration of rhodamine DSPE liposome enclosed alendronate (1.5 mg/kg).

FIGS. 11a-b are images captured by confocal microscopy of brain sections twenty four hours following intravenous (I.V.) administration of rhodamine DSPE liposome enclosed alendronate (1.5 mg/kg).

FIGS. 12a-b are images captured by confocal microscopy of brain sections five days following intravenous (I.V.) administration of rhodamine DSPE liposome enclosed alendronate (1.5 mg/kg).

FIGS. 13a-b are images captured by confocal microscopy of spinal cord sections four hours following intravenous (I.V.) administration of rhodamine DSPE liposome enclosed alendronate (1.5 mg/kg).

FIGS. 14a-b are images captured by confocal microscopy of spinal cord sections twenty four hours following intravenous (I.V.) administration of rhodamine DSPE liposome enclosed alendronate (1.5 mg/kg).

FIGS. 15a-b are images captured by confocal microscopy of spinal cord sections five days following intravenous (I.V.) administration of rhodamine DSPE liposome enclosed alendronate (1.5 mg/kg).

DESCRIPTION OF THE PREFERRED EMBODIMENTS

Figure 1:
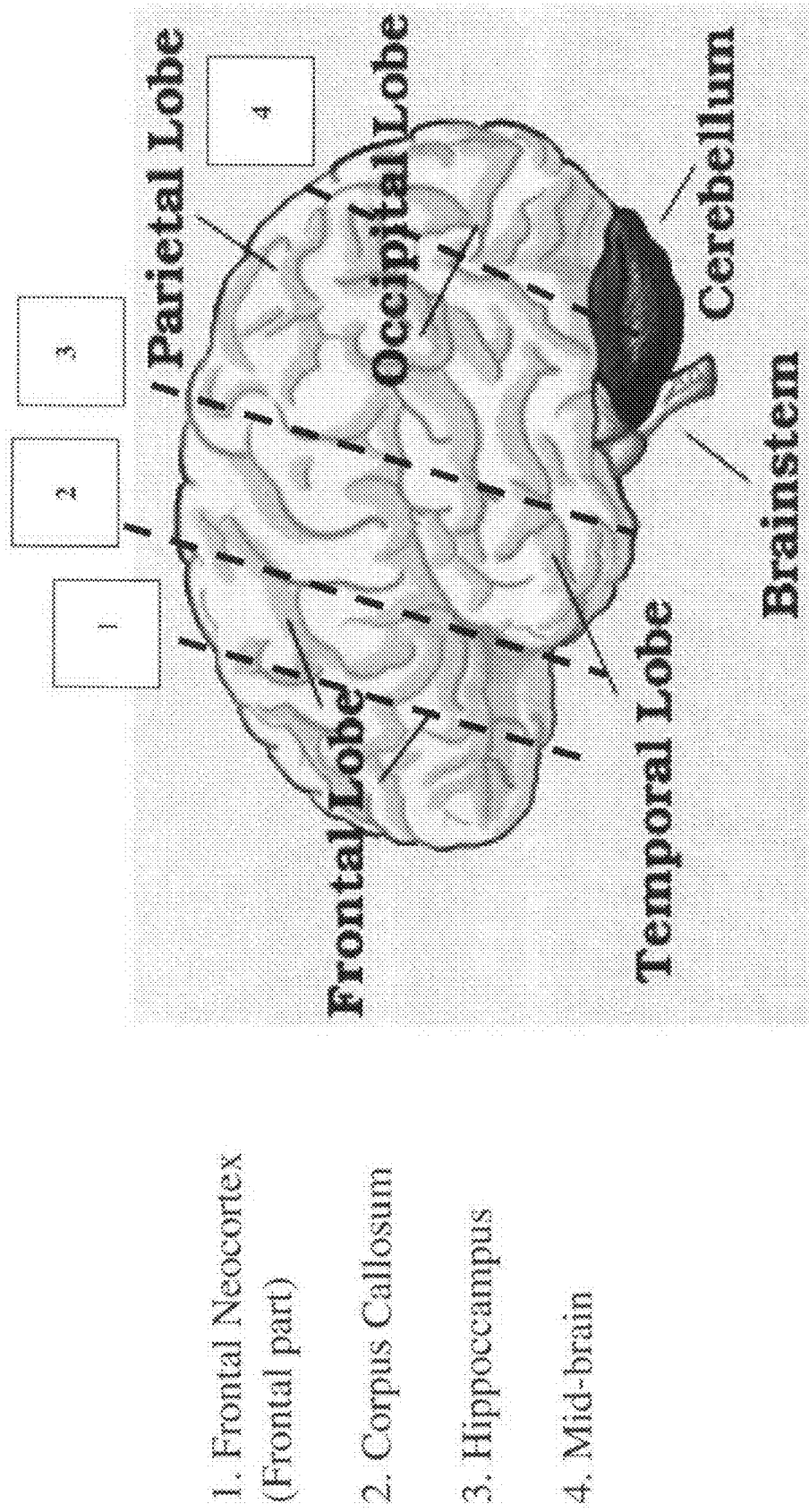
FIG. 1 is an annotated diagram of the brain sections analyzed by confocal microscopy as described in Examples 1 and 2.

The present invention relates to a method and pharmaceutical compositions for delivering a pharmaceutical agent into a target organ which is protected by a blood barrier and, more particularly, to the delivery of pharmaceutical agents to the brain.

The principles and operation of delivering pharmaceutical agents across a blood barrier according to the present invention may be better understood with reference to the examples and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The blood-brain barrier prevents many compounds in the blood stream from entering the tissues and fluids of the brain. Nature provides this mechanism to ensure a toxin-free environment for neurologic function. However, it also prevents delivery to the brain of therapeutic compounds, such as neuropharmaceuticals, potential neuropharmaceuticals, and other active agents, that might otherwise remedy or modify neurologically-related activities and other brain indications.

Today, non-surgical treatments of neurologic disorders are limited to systemic introduction of compounds through the blood stream. A drawback of this form of treatment is the relatively small number of known compounds that pass through the blood-brain barrier. Even those that do cross the barrier often produce adverse reactions in other parts of the body or in non-targeted regions of the brain. Prior art surgical treatments of neurologic disorders are typically limited to removal or ablation of non-integrated brain tissue. While these treatments have proven effective for certain localized disorders, such as tumors, they involve delicate, time-consuming procedures that may result in destruction of otherwise healthy tissues.

While searching liposome formulations for killing cells of the MPS for the prevention of restenosis, the present inventors have unexpectedly and surprisingly found that liposomes which are formulated so that they are avidly taken up by cells of the MPS, yet have no toxic effect thereupon are able to cross the BBB and enter the brain and spinal cord. The present invention exploits this finding to provide a novel delivery system of pharmaceutical agents across a blood barrier.

As is illustrated herein below and in the Examples section which follows, liposome-loaded cells of the MPS were able to cross rabbit BBB and penetrate the spinal cord and brain tissue as indicated by the presence of hydrophobic and hydrophilic markers suggesting that both the liposome core and membrane cross the BBB (see Example 1). BBB penetration was MPS dependent as it was inhibited by alendronate (see Example 2).

U.S. Pat. No. 6,096,716 discusses the use of liposomes for transferring nucleic acids into central nervous system cells both in vivo and in vitro. However, in sharp contrast to the present invention, these liposomes do not cross the blood brain barrier, but rather are administered directly to the brain. The liposomes of the present invention do cross the blood brain barrier and therefore can be administered parenterally.

PCT Application, Publication No. WO9402178A1 and Huitinga et al., [J exp Med 172, 1990, 1025-33] both discuss the use of modified liposomes for crossing the blood brain barrier. The liposomes used therein are formulated to avoid phagocytosis by the cells of the MPS. The liposomes of the present invention are unmodified and in sharp contrast to PCT Application, Publication No. WO9402178A1 and Huitinga et al., rely on their formulation such that they are avidly taken up by cells of the MPS.

U.S. Pat. Appl. No. 20040266734 and U.S. Pat. Appl. No. 20040265391 both describe a similar formulation of liposomes to the present invention for the treatment of restenosis and acute coronary syndromes, containing pharmaceutical agents which are toxic to cells of the MPS, thereby teaching away from the present invention. In contrast to U.S. Pat. Appl. No. 20040266734 and U.S. Pat. Appl. No. 20040265391, the liposomes of the present invention are administered such that the pharmaceutical agent is sequestered within the particles until reaching its target organ, and thus has no therapeutic or toxic effect on the carrier cells of the MPS themselves.

Rousseau et al, 1999 supra discusses the possibility that cells of the MPS may transport liposomes across the blood brain barrier, but in contrast to the present invention, Rousseau's system necessitates a disrupted blood brain barrier for liposome penetration. In fact, in the method described by Rousseau, the liposomes did not penetrate brain areas, but remained confined to the region of the blood barrier.

Pat. Appl. No. 20050048002 discusses the use of phagocytic cells as carriers of solid particles which contain within them (suspended precipitates) of pharmaceutical agents to the brain. The solubility of the pharmaceutical agent described therein is "poorly water soluble". In sharp contrast to the present application, Pat. App. No. 20050048002 does not contemplate the use of pharmaceutical agents encapsulated in liquid liposomes as a method of delivery across a blood barrier. An advantage of using liposomes is that these carriers enable water soluble as well as completely insoluble pharmaceutical agents to be formulated (as described herein below) without the use of surfactants or other emulsifiers, eliminating the drawbacks associated with the use of such. Also, using liposomes and not other particle types, it is possible to formulate both a water soluble and insoluble pharmaceutical agent into the same liposome by incorporating them in the hydrophilic core or the hydrophobic shell respectively. Not only are the particle type and the formulation thereof of Pat. Appl. No. 20050048002 different from the present invention, but the present invention allows targeting to all blood barrier protected organs including the brain, eyes, mammary glands and testicles.

Thus, according to one aspect of the present invention there is provided a method of delivering a pharmaceutical agent into a target organ protected by a blood barrier. The method is effected by administering to a subject in need thereof an amount of liposomes which comprise the pharmaceutical agent. The amount and formulation of the liposomes are selected such that liposomes accumulate in cells of an immune system of the subject to thereby generate liposome loaded immune cells. Once the liposomes enter the immune cells, the latter become activated and cross the blood barrier, releasing an effective amount of the pharmaceutical agent from the liposomes in the target organ of the subject.

As used herein the phrase "target organ protected by a blood barrier" refers to the brain, eye, mammary and testicle each of which are characterized by specialized cellular features including, but not limited to the presence of tight junctions and several specific markers such as the glucose transporter, P-glycoprotein, and -glutamyl transpeptidase.

As used herein, the phrase "cells of an immune system" are cells which constitute the cellular immune response and are capable of phagocytosis such as those belonging to the mononuclear phagocytic system, (MPS), including, but not limited to macrophages and monocytes. Other cells of an immune system capable of phagocytosis include neutrophils, eosinophils and basophils.

The term "phagocytosis" as used herein refers to a preferred means of entry into a phagocytic cell. It also encompasses forms of endocytosis, including but not limited to pinocytosis, receptor-mediated endocytosis and other cellular means for absorbing/internalizing material from outside the immune cells of the present invention.

It will be appreciated that following phagocytosis, the macrophages and/or monocytes become activated. As used herein, the term "activated" is reserved for macrophages and/or monocytes possessing specifically increased functional activity after being primed by a liposomal particle. For this invention, it is important that the phagocytic cells are not preactivated by another agent e.g., by LPS, prior to administration of the liposomes comprising the pharmaceutical agent.

As used herein the phrase "subject in need thereof" refers to a mammal, preferably a human subject, which suffers from, or may be predisposed to (i.e., at risk of suffering from) an indication affecting blood protected organs, as further described hereinbelow. Examples of non-human mammals include, but are not limited to, mouse, rat, rabbit, bovine, porcine, ovine, canine and feline.

As used herein the phrase "pharmaceutical agent" refers to a therapeutic or diagnostic agent which can be used to treat or diagnose an indication (as further described hereinbelow) of a blood barrier protected organ, respectively.

As used herein the term "liposomes" refers to fully closed carrier molecules comprising a spherical lipid membrane which itself is in a liquid crystalline phase or a liquid gel phase, in which an entrapped liquid volume is contained. The two liquid phases are immiscible. Thus, liposomes of the present invention, similar to membranes of cells, are in an entirely gel/liquid state and/or liquid crystal state and not in a solid state.

Liposomes include niosomes, transfersomes, emulsions, foams, micelles, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43].

Any method known in the art can be used to incorporate a pharmaceutical agent into a liposome. For example, the pharmaceutical agent may be encapsulated within the liposome. Alternatively, it may be adsorbed on the liposome's surface. Other methods that may be used to incorporate a pharmaceutical agent into a liposome of the present invention are those described by Alfonso et al., [The science and practice of pharmacy, Mack Publishing, Easton Pa. 19th ed., (1995)] and those described by Kulkarni et al., [J. Microencapsul. 1995, 12 (3) 229-46].

The liposomes comprising pharmaceutical agents should be formulated to sequester the pharmaceutical agents for a sufficient time to enhance delivery of the agent to the phagocytic cell and ensure that it remains sequestered within the cells of the immune system until it reaches its target site (e.g., brain, retina, testicle and mammary), after which the pharmaceutical agent is released due to dissolution of the liposomes within the macrophages. This is particularly significant where the pharmaceutical agent (e.g., cytotoxic agents) may affect the carrier immune cells themselves. In these cases, the use of a more stable liposome formulation may be required. For example incorporation of a certain amount of cholesterol in liposomes results in a decrease of their intracellular degradation by macrophages. It has also been shown that the addition of cholesterol to the liposome formulation increases the sequestering efficiency of the liposome by about two fold [Mumper et al., AAPS PharmSciTech, 2000; 1 (1) article 3].

It is envisaged, that a few hours (e.g., 4 hours) delay in the intracellular degradation of the liposome should suffice to produce sufficient drug levels to the target organ.

Methods of stabilizing liposomes are known in the art including those disclosed in U.S. Pat. Application Nos. 20040156890, 20040072992 and 20020058060.

The liposomes used in the methods of the present invention specifically cross blood barriers by way of their composition which is taken up by only particular cell types (e.g., macrophages and/or monocytes). In preferred embodiments, the specificity of the liposome for phagocytic cells is due to its physiochemical properties, e.g., size or charge, such that it can only, or primarily be internalized by phagocytosis. In contrast, non-phagocytic cells are incapable of taking up the liposome due to its large dimension and/or other physiochemical properties. Preferably, the liposomes of the present invention do not comprise a blood barrier targeting polysaccharide (e.g. mannose) in their membrane portion. Preferably, the liposomes of the present invention do not comprise peptides in their membrane portion that target the liposomes to a receptor on a blood barrier. Examples of such peptides include but are not limited to transferrin, insulin, IGF-1, IGF-2 anti-transferrin receptor antibody, anti-insulin receptor antibody, anti-IGF-1 receptor antibody and anti-IGF-2 receptor antibody.

As mentioned, liposomes containing one or more pharmaceutical agent of this aspect of the present invention can be prepared so that the size of the liposome is large enough to primarily be internalized by phagocytosis, thus imparting specificity to phagocytic cells. As such, other cells which are not capable of phagocytosis will not be affected by the liposomes of the present invention. Liposomes of the present invention of less than 1.0 µm are typically used to avoid side effects (such as disruption of the BBB, blockage of the lungs, blockage of alveolar and pulmonary blood vessels, and complement activation). Liposomes of the present invention of larger than 0.07 µm are typically used to avoid their escape from phagocytosis. Liposomes comprising one or more pharmaceutical agent of the present invention are preferably in the size range of 0.02-1.0 µm, more preferably 0.05-1.0 µm, more preferably 0.07-0.5 µm and more preferably 0.1-0.3 µm. An advantage of liposomes smaller or about 0.2 µm is that they can easily undergo filter sterilization.

Any method known in the art can be used to determine the size of the liposome. For example, a Nicomp Submicron Particle Sizer (model 370, Nicomp, Santa Barbara, Calif.) utilizing laser light scattering can be used. Other methods of measuring liposome size include photocorrelation spectroscopy, laser diffraction, low-angle laser light scattering (LALLS), medium-angle laser light scattering (MALLS), light obscuration methods (Coulter method, for example), rheology, or microscopy (light or electron). The preferred average effective particle size depends on factors such as the intended route of administration, formulation, solubility, toxicity and bioavailability of the compound.

For sizing liposomes, homogenization may be used, which relies on shearing energy to fragment large liposomes into smaller ones. Homogenizers which may be conveniently used include microfluidizers produced by Microfluidics of Boston, Mass. In a typical homogenization procedure, liposomes are recirculated through a standard emulsion homogenizer until selected liposomes sizes are observed. The well-known sonication technique can also be used for sizing down and homogenization. Extrusion of liposomes through a commercially available polycarbonate membrane (eg. from Sterlitech, Wash.) or an asymmetric ceramic membrane (e.g., Membralox), commercially available from Pall Execia, France is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

The liposomes of this aspect of the present invention preferably have a charged surface (i.e., positively charged or negatively charged). Preferably, the charged surface is a negatively charged surface. Preferably, the negatively charged surface comprises negatively charged lipids such as dicetyl phosphate or dioleoyl-1,2-diacyl-3-trimethylammonium-propane (DOTAP) or other negatively charged membrane constituents) such as phospholipids, including, but not limited to phosphatidylserine, phosphatidic acid, and phosphatidyl glycerol (for example DSPG).

Typically the liposomes of the present invention are hydrophobic since hydrophilic masking of the liposome membrane (e.g., by use of polyetheleneglycol-linked lipids and hydrophilic particles) may be less prone to MPS uptake. It is also typical that the liposomes do not comprise sterically shielded lipids such as ganglioside-$GM_1$ and phosphatidylinositol since these lipids prevent MPS uptake. Since inclusion of cholesterol in the liposome enhances uptake by the MPS [Ahsan, F. et al., 2002, Journal of controlled Release, 79, 29-40], typically the liposomes of the present invention include cholesterol.

As detailed above, many properties influence uptake of the liposomes by phagocytic cells including, but not limited to liposome size, charge and hydrophobicity, as well as the phospholipids and non-phospholipid components of the liposome.

In order to determine liposomes that are especially suitable in accordance with the present invention a screening assay can be performed such as the assays described in U.S. Pat. Appl. No. 20040266734 and U.S. Pat. Appl. No. 20040265391; and in Danenberg et al., Journal of cardiovascular pharmacology 2003, 42:671-9; Circulation 2002, 106:599-605; Circulation 2003, 108:2798-804. In the in vitro screening assay, liposome uptake is examined on tissue culture of macrophages. The phagocytic cells may be obtained from an established cell line or recently isolated from an individual as a primary cell line. The liposomes may be formulated such that they contain markers e.g. fluorescent markers, as described in the Example section herein below so that uptake may be followed by microscopy. In the in vivo assay liposome uptake is examined following FACS analysis of fluorescent markers of rabbit blood following IV injection of the liposomal formulations.

The liposomes may be modified in any other way to enhance their uptake by the phagocytic cells, e.g. by attaching to them molecules recognized selectively by phagocytic cells such as ligands that interact with the macrophage Fc receptor, or galactosyl ligands, or inclusion of substances in the bilayer such as complement fibronectin lipoproteins or gamma globulin.

The ability of the liposomes of the present invention to accumulate in the phagocytic cell is also influenced by the amount of the administered liposome particle. Determination of the optimal amount, size and formulation of a liposome to cross a blood barrier can be carried out using procedures known in the art. For example, liposomes may be formulated such that they contain fluorescent markers, e.g., the hydrophilic marker 1-Hydroxypyren-3,6,8-Trisulfonic acid and the hydrophobic marker Rhodamin-DSPE as in the Examples section herein below. The liposomes may be administered to a test subject (e.g. mouse, rabbit) and after a set amount of time the target organ is optionally removed and examined using confocal microscopy (for further description see Example 1 of the Examples section, which follows).

As mentioned, liposome formulations may be selected such that the pharmaceutical agent remains encapsulated or sequestered in the phagocytic cell according to the needs of the patient. For example, the time a phagocytic cell requires to cross the testicular blood barrier may be longer or shorter than the time the phagocytic cell requires to cross the blood brain barrier. Therefore, if a therapeutic agent is an anti-cancer drug for the treatment of testicular cancer, the formulation of the liposome should take these kinetic considerations into account ensuring that it is targeted to the testicles and not the brain. This increases the specificity of delivery to the target site and avoids unnecessary side effects. The liposomes are released from the phagocytic cells either actively (e.g. exocytosis) or passively (e.g. disintegration of the cell membrane). Furthermore, liposomes of the pharmaceutical agents may discharge the pharmaceutical agent from the particles when they are at the target site either actively, e.g. by a change in pH or temperature or passively e.g. by leakage.

The composition of the liposomes (e.g. unilamellar or multilamellar) of this aspect of the present invention may be formulated according to the pharmaceutical agent which is to be delivered. Thus, if the pharmaceutical agent is hydrophilic, its delivery may be further improved using large unilamellar vesicles because of their greater internal volume. Conversely, if the pharmaceutical agent is hydrophobic, its delivery may be further improved using multilamellar vesicles. Alternatively, if the pharmaceutical agent (e.g. oligonucleotide) is not able to penetrate the lipid bilayer, it may remain adsorbed to the liposome surface. In this case, increasing the surface area of the liposome may further improve delivery of the pharmaceutical agent. If a combination of pharmaceutical agents of varying water solubility is to be formulated in the same liposome, an appropriate balance is struck between the quantity of phospholipids and the aqueous internal volume. The method of the present invention is thus particularly suitable for the administration of a combination of pharmaceutical agents of varying water solubility.

As mentioned the pharmaceutical agent of the present invention is selected to treat or diagnose a pathology of blood barrier protected organs.

Examples of brain indications which may be treated or diagnosed by the agents of the present invention include, but are not limited to brain tumor, neuropathy, Alzheimer's disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, bacterial infection, fungal infection, stroke, aging, dementia, schizophrenia, depression, manic depression, anxiety, panic disorder, social phobia, sleep disorder, attention deficit, conduct disorder, hyperactivity, personality disorder, drug abuse, infertility and head injury.

Examples of eye indications which may be treated or diagnosed by the agents of the present invention include age related macular degeneration and diabetic retinopathy.

Examples of testicle indications which may be treated or diagnosed by the agents of the present invention include testicular cancer and any form of testicular trauma.

An example of a mammary gland indication which may be treated or diagnosed by the agents of the present invention is mastitis.

It will be appreciated that the method of the present invention is useful for treating diseases in which the BBB is intact, since no prior disruption of the BBB is required for delivering the pharmaceutical agents according to the method of the present invention. However, it can also be used to treat indications where the BBB is altered.

Leukocyte transendothelial migration across a disrupted BBB is a prominent feature of many neurodegenerative disorders. Marked changes in BBB function is observed in several neurological disorders associated with immune responses such as MS, meningitis, and HIV-1-associated dementia. Similar permeability changes in the retinal blood barrier are observed with age related macular degeneration and diabetic retinopathy.

As mentioned, the pharmaceutical agent may be a therapeutic agent or a diagnostic agent.

Examples of therapeutic agents include, but are not limited to, inorganic or organic compounds; small molecules (i.e., less than 1000 Daltons) or large molecules (i.e., above 1000 Daltons); biomolecules (e.g. proteinaceous molecules, including, but not limited to, peptide, polypeptide, post-translationally modified protein, antibodies etc.) or a nucleic acid molecule (e.g. double-stranded DNA, single-stranded DNA, double-stranded RNA, single-stranded RNA, or triple helix nucleic acid molecules) or chemicals. Therapeutic agents may be natural products derived from any known organism (including, but not limited to, animals, plants, bacteria, fungi, protista, or viruses) or from a library of synthetic molecules. Therapeutic agents can be monomeric as well as polymeric compounds.

As mentioned above, the therapeutic agent may be a protein, such as an enzyme which compensates for loss in activity or poor expression of an endogenous enzyme e.g., the enzyme hexosaminidase A, a shortage of which results in Tay-Sachs disease.

Examples of therapeutic agents which may be delivered across a blood barrier to the brain, eye, testis or mammary gland include, but are not limited to antibiotic agents, anti-neoplastic agents, anti-inflammatory agents, antiparasitic agents, antifungal agents, antimycobacterial agents, antiviral agents, anticoagulant agents, radiotherapeutic agents, chemotherapeutic agents, cytotoxic agents, vasodilating agents, and anti-oxidants.

Additional therapeutic agents which may be delivered to the brain across the blood brain barrier according to this aspect of the present invention include, but are not limited to, analeptic agents, anti-convulsant agents, antihistamine agents, neurotrophic agents, psychotherapeutic agents, anxiolytic sedative agents, stimulant agents, sedative agents, analgesic agents, anesthetic agents, birth control agents, neurotransmitter agents, neurotransmitter analog agents, scavenging agents and fertility-enhancing agents.

Examples of neurotransmitter agents which can be used in accordance with the present invention include but are not limited to acetycholine, dopamine, norepinephrine, serotonin, histamine, epinephrine, Gamma-aminobutyric acid (GABA), glycine, glutamate, adenosine, inosine and aspartate.

Neurotransmitter analog agents include neurotransmitter agonists and antagonists. Examples of neurotransmitter agonists that can be used in the present invention include, but are not limited to almotriptan, aniracetam, atomoxetine, benserazide, bromocriptine, bupropion, cabergoline, citalopram, clomipramine, desipramine, diazepam, dihydroergotamine, doxepin duloxetine, eletriptan, escitalopram, fluvoxamine, gabapentin, imipramine, moclobemide, naratriptan, nefazodone, nefiracetam acamprosate, nicergoline, nortryptiline, paroxetine, pergolide, pramipexole, rizatriptan, ropinirole, sertraline, sibutramine, sumatriptan, tiagabine, trazodone, venlafaxine, and zolmitriptan.

Examples of neurotransmitter antagonist agents that can be used in the present invention include, but are not limited to 6 hydroxydopamine, phentolamine, rauwolfa alkaloid, eticlopride, sulpiride, atropine, promazine, scopotamine, galanin, chlopheniramine, cyproheptadine, dihenylhydramine, methyl sergide, olanzapine, citalopram, fluoxitine, fluoxamine, ketanserin, oridanzetron, p chlophenylalanine, paroxetine, sertraline and venlafaxine.

Particularly useful in the present invention are therapeutic agents such as peptides (e.g., neuropeptides) which have specific effects in the brain but which under normal conditions poorly penetrate the blood brain barrier, and have no or little effect in other organs. These compounds are often readily broken down in the bloodstream, and thus would benefit from the protection provided by encapsulation in a liposome. It has been shown that only small quantities of peptides are required in the brain to provide a desired pharmacological effect.

The term "neuropeptides" as used herein, includes peptide hormones, peptide growth factors and other peptides. Examples of neuropeptides which can be used in accordance with the present invention include, but are not limited to Oxytocin, Vasopressin, Corticotropin releasing hormone (CRH), Growth hormone releasing hormone (GHRH), Luteinizing hormone releasing hormone (LHRH), Somatostatin growth hormone release inhibiting hormone, Thyrotropin releasing hormone (TRH), Neurokinin a (substance K), Neurokinin β, Neuropeptide K, Substance P, β-endorphin, Dynorphin, Met- and leu-enkephalin, Neuropeptide tyrosine (NPY), Pancreatic polypeptide, Peptide tyrosine-tyrosine (PYY), Glucogen-like peptide-1 (GLP-1), Peptide histidine isoleucine (PHI), Pituitary adenylate cyclase activating peptide (PACAP), Vasoactive intestinal polypeptide (VIP), Brain natriuretic peptide, Calcitonin gene-related peptide (CGRP) (α- and β-form), Cholecystokinin (CCK), Galanin, Islet amyloid polypeptide (IAPP), Melanin concentrating hormone (MCH), Melanocortins (ACTH, α-MSH and others), Neuropeptide FF, Neurotensin, Parathyroid hormone related protein, Agouti gene-related protein (AGRP), Cocaine and amphetamine regulated transcript (CART)/peptide, Endomorphin-1 and -2, 5-HT-moduline, Hypocretins/orexins Nociceptin/orphanin FQ, Nocistatin, Prolactin releasing peptide, Secretoneurin and Urocortin Examples of therapeutic agents suitable for delivery across a blood retina barrier include, but are not limited to those that are used to treat age related macular degeneration and diabetic retinopathy.

Examples of therapeutic agents suitable for delivery across a blood testis barrier include, but are not limited to those that are used to treat testicular cancer and any form of testicular trauma.

Examples of therapeutic agents suitable for delivery across a blood mammary barrier include, but are not limited to those that are used to treat mastitis.

As mentioned above, the present invention envisages the administration of one or more therapeutic agent loaded liposomes to manage or treat an indication mentioned herein above. The loaded particles themselves may contain more than one therapeutic agent. Alternatively, therapeutic agents may be administered in combination to the subject where each liposome is loaded with one therapeutic agent only.

As mentioned, the present invention may be used to deliver diagnostic agents to blood protected organs. Examples of diagnostic agents which can be used in accordance with the present invention include the x-ray imaging agents, fluorescent imaging agents and contrast media. Examples of x-ray imaging agents include WIN-8883 (ethyl 3,5-diacetamido-2,4,6-triiodobenzoate) also known as the ethyl ester of diatrizoic acid (EEDA), WIN 67722, i.e., (6-ethoxy-6-oxohexyl-3,5-bis(ace-tamido)-2,4,6-triiodo-benzoate; ethyl-2-(3,5-bis(acetamido)-2,4,6-triiodo-b-enzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyl-oxy malonate (WIN 67721); ethyl 2-(3,5-bis(acetamido)-2,4,6-triiodobenzoyl-oxy) phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Other contrast media include, but are not limited to, magnetic resonance imaging aids such as gadolinium chelates, or other paramagnetic contrast agents. Examples of such compounds are gadopentetate dimeglumine (Magnevist®) and gadoteridol (Prohance®). Patent Application No. 20010001279 describes liposome comprising microbubbles which can be used as ultrasound contrast agents. Thus, diagnostic contrast agents can also be used in corporation with the present invention for aiding in ultrasound imaging of the brain.

Labeled antibodies may also be used as diagnostic agents in accordance with this aspect of the present invention. Use of labeled antibodies is particularly important for diagnosing diseases such as Alzheimer's where presence of specific proteins (e.g., β amyloid protein) are indicative of the disease.

A description of classes of therapeutic agents and diagnostic agents and a listing of species within each class can be found in Martindale, The Extra Pharmacopoeia, Twentyninth Edition, The Pharmaceutical Press, London, 1989 which is incorporated herein by reference and made a part hereof. The therapeutic agents and diagnostic agents are commercially available and/or can be prepared by techniques known in the art.

The pharmaceutical agent-loaded liposomes of the present invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the therapeutic agent or diagnostic agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

The concentration of the liposomes in these formulations can vary widely, i.e., from less than about 0.5%, usually at or at least about it to as much as 15 or 20% by weight and will be selected primarily by fluid volumes, viscosities, etc., in accordance with the particular mode of administration selected. Actual methods for preparing parenterally administrable liposomes formulations will be known or apparent to those skilled in the art and are described in detail in, for example, Remington's Pharmaceutical Science 17th ed., Mack Publishing company, Easton, Pa. (1985).

Any route of administration may be taken provided that the liposomes become in contact with cells of the immune system. For example, suitable routes of administration include oral, rectal, transmucosal, especially transnasal, intestinal or parenteral delivery, including intramuscular, subcutaneous injections as well as direct intraventricular, intravenous, intraperitoneal and intranasal injections.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

Pharmaceutical compositions suitable for use in context of the present invention include compositions wherein the active ingredients are contained in an amount effective to achieve the intended purpose. More specifically, a therapeutically effective amount means an amount of active ingredients (therapeutic drug) effective to prevent, alleviate or ameliorate symptoms of a disorder (e.g., brain tumor) or prolong the survival of the subject being treated. It should be understood that for an active agent to be therapeutically available to an organ protected by a barrier, preferably no less than 5% of the active agent should be discharged at the target site, more preferably no less than 4%, more preferably no less than 3%, more preferably no less than 2%, more preferably no less than 1%, more preferably no less than 0.5% and most preferably no less than 0.1% of the active agent should be discharged at the target site.

A diagnostically effective amount is an amount of active ingredients (diagnostic agent) that allows diagnosis of a disorder (including the presence, stage or treatment regime required).

Determination of a therapeutically and diagnostically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Detection of Liposomes in the Brain

A particular liposome formulation was tested for crossing the blood barrier of rabbit brain.
Materials and Methods
Materials
DSPC, DSPG (Avanti Polar Lipids, Alabaster, Ala.) and cholesterol (Sigma, St. Louis, Mo.); Extruder—Lipex Biomembranes, Vancouver, Canada; Polycarbonate filters—Whatman international Ltd., Madistone Kent, UK; 1-Hydroxypyren-3,6,8-Trisulfonic acid (Sigma, St. Louis, Mo.); Rhodamin-DSPE (Avanti Polar Lipids, Alabaster, Ala.); O.C.T compound (Sakura Finetek U.S.A., Inc Torrance, Calif. 90501 USA); Confocal microscopy—laser confocal scanning microscopy, Zeiss modal 410, Gena, Germany;

Alendronate—CIPLA LTD, Mahesh Hiremath, Mumbai-400 008, INDIA (from Biorest); Sephadex G-50—(Sigma, St. Louis, Mo.).

Liposome Preparation

Liposomes were prepared by thin lipid film hydration. DSPC, DSPG, and Cholesterol (3:1:2) were dissolved in t-butanol and lyophilized overnight. The lyophilized cake was hydrated with an aqueous solution at 55-60° C. and left to stand for 1 hour at the same temperature. The suspension was then extruded three times through double polycarbonate membranes of 0.8, 0.4 and 0.2 µm pore sizes (Nucleopore), by means of extruder. Liposomes were passed through a Sephadex G-50 column and eluted in MES/HEPES buffer ph 7.2 (50 mM MES, 50 mM HEPES, 75 Mm NaCl) to remove un-encapsulated marker.

Liposomes of the same formulation were prepared and sized containing three different fluorescent markers:
a. liposomes containing the hydrophilic marker 1-Hydroxypyren-3,6,8-Trisulfonic acid were sized at 197±38 nm;
b. liposomes containing the hydrophobic marker Rhodamin-DSPE were sized at 210±37 nm;
c. liposomes containing both 1-Hydroxypyren-3,6,8-Trisulfonic acid and Rhodamin-DSPE were sized at 206±25 nm.

Animal Treatment

New Zealand White male rabbits, 2.5-3.5 kg (body weight) were administered with the above liposomes at a dose of 1.5 ml/kg by intravenous injection and sacrificed one or four hours following injection.

Specimen Preparation

The rabbits were perfused with 200-250 ml PBS prior to spinal cord excision (post the border of the medulla oblongata (between C1 to C2)) and brain removal as shown in FIG. 1 (frontal neocortex (frontal part), corpus callosum, hippocampus and mid brain)). The brains and spinal cords were harvested and fixed (3.7% formalin/PBS) for 10 minutes (37% formalin diluted with PBS 1:10, to a final concentration of 3.7%). The fixed brains and spinal cords were embedded in OCT compound, placed into plastic molds and frozen at −70° C. 8-10 µm tissue slices were cut using a cryotome at −20° C. and fixed on slides after which they were rinsed with PBS for 5 minutes. Finally, slides were mounted using mounting solution (80% glycerol/20% PBS) and sealed with nail polish. Slides were analyzed using confocal microscopy.

Results

As can be seen in FIGS. 2a-9b, the liposomes cross the blood brain barrier and penetrate spinal cord and brain tissue. Both the hydrophobic (Rhodamin-DSPE) and hydrophilic (1-Hydroxypyren-3,6,8-Trisulfonic acid) markers can be detected indicating that both the liposomal core and membrane cross the blood brain barrier. Staining of the tissues can be seen one hour following liposome administration and also four hours following administration.

Example 2

Detection of Liposomes in the Brain after Liposomal Alendronate Administration

The aim of this experiment was to determine whether liposomal penetration of the blood brain barrier requires activated/live monocytes by the administration of liposome enclosed alendronate. Alendronate is known to deplete circulating monocytes and/or deactivate them.

Materials and Methods

Liposome Preparation

Liposome enclosed alendronate, approximately 200 nm in diameter, was prepared by thin lipid film hydration. DSPC, DSPG, and Cholesterol (3:1:2) were dissolved in t-butanol and lyophilized over night. The lyophilized cake was hydrated with an aqueous solution containing alendronate at 55-60° C. and left to stand for 1 hr at the same temperature. The suspension was then extruded three times through double polycarbonate membranes of 0.8, 0.4, and 0.2 µm pore sizes (Nucleopore), by means of extruder. Liposomes were passed through a Sephadex G-50 column and eluted in MES/HEPES buffer ph 7.2 (50 mM MES, 50 mM HEPES, 75 Mm NaCl) to remove un-encapsulated drug/marker.

Animal Treatment

New Zealand White male rabbits, 2.5-3.5 kg body weight were injected IV with 1.5 ml/kg of liposome enclosed alendronate (labeled with the fluorescent marker, Rhodamine—DSPE). The rabbits were sacrificed 4 hours, 24 hours and 5 days following injection.

Specimen Preparation

As detailed in Example 1 above;

Results

As can be seen in FIGS. 10a-15b liposome enclosed alendronate does not penetrate the BBB.

CONCLUSION

When monocytes are inactivated/depleted by the liposomal alendronate treatment there is no passage of the liposomes to the brain. Thus, there is a need of live as well as activated monocytes in order to penetrate the BBB.

From these results, a mechanism for a delivery system across a blood brain barrier can be suggested. Liposomal delivery of a pharmaceutical agent induces activation of the immune system, resulting in efficient uptake of the loaded vesicles by the circulating MPS and subsequent brain uptake.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of delivering a pharmaceutical agent into an organ protected by a blood barrier, the method comprising:
administering to a blood stream of a subject an amount of liposomes comprising the pharmaceutical agent not toxic to monocyte cells such that the monocyte cells circulating in the blood stream are not depleted, said liposomes being about 0.05 to 1.0 µm in diameter, wherein an amount of said liposomes accumulate in the monocyte cells of said subject by phagocytosis to thereby generate liposome loaded monocyte cells, said liposome loaded monocyte cells crossing the blood barrier and delivering said pharmaceutical agent to said organ, wherein said liposomes do not comprise in a membrane portion a blood barrier targeting ligand that targets the liposomes to a receptor on the blood barrier.

2. The method of claim 1, wherein the pharmaceutical agent is encapsulated within the liposomes.

3. The method of claim 1, wherein the pharmaceutical agent is adsorbed on a surface of the liposomes.

4. The method of claim 1, wherein the pharmaceutical agent is a therapeutic agent.

5. The method of claim 1, wherein the pharmaceutical agent is a diagnostic agent.

6. The method of claim 1, wherein the liposomes are about 0.07 to 0.5 µm in diameter.

7. The method of claim 1, wherein the liposomes are about 0.1 to 0.3 µm in diameter.

8. The method of claim 1, wherein the liposomes are less than about 0.2 µm in diameter.

9. The method of claim 1, wherein the blood brain barrier is not disrupted.

10. The method of claim 1, wherein the liposomes are non-mannosylated.

\* \* \* \* \*